United States Patent [19]

Kurono et al.

[11] Patent Number: 4,535,075
[45] Date of Patent: Aug. 13, 1985

[54] DITHIOLANE DERIVATIVE, PROCESS FOR PRODUCING THE SAME AND USE THEREOF

[75] Inventors: Hitoshi Kurono, Toyonaka; Kuniaki Taninaka, Neyagawa; Tatsuyoshi Sugimoto, Hashimoto; Minoru Katoh, Fujiidera, all of Japan

[73] Assignee: Nihon Nohyaku Co., Ltd., Tokyo, Japan

[21] Appl. No.: 506,830

[22] Filed: Jun. 22, 1983

[30] Foreign Application Priority Data

Jun. 28, 1982 [JP] Japan .................. 57-111182

[51] Int. Cl.$^3$ .................. C07D 495/04; C07D 339/09; A61K 31/38; A61K 31/285
[52] U.S. Cl. .......................... 514/96; 549/32; 549/35; 514/99
[58] Field of Search ...................... 349/35, 32; 424/277

[56] References Cited
U.S. PATENT DOCUMENTS 4,080,466 3/1978 Taninaka et al. .................. 424/277

*Primary Examiner*—Robert T. Bond

*Attorney, Agent, or Firm*—Cushman, Darby & Cushman

[57] ABSTRACT

Dithiolane derivatives represented by the formula (I):

$$\begin{array}{c} HOCH-S \\ | \\ HOCH-S \end{array} C=C \begin{array}{c} R^2 \\ \\ COR^1 \\ \parallel \\ O \end{array} \quad (I)$$

wherein $R^1$ is an alkyl group, a cycloalkyl group, an alkenyl group, an alkynyl group, a benzyl group or an alkoxyalkyl group and $R^2$ is a cyano group, an alkylcarbonyl group, a benzylcarbonyl group, a phenylcarbonyl group, an alkoxycarbonyl group, a cycloalkyloxycarbonyl group, a benzyloxycarbonyl group, an alkenyloxycarbonyl group, an alkynyloxycarbonyl group or an alkoxyalkoxycarbonyl group, and an organic acid ester thereof; process for producing the same; and pharmaceutical composition for controlling liver diseases of human beings and animals containing the same.

40 Claims, No Drawings

DITHIOLANE DERIVATIVE, PROCESS FOR PRODUCING THE SAME AND USE THEREOF

The present invention relates to a dithiolane derivative and an organic acid ester thereof, a process for producing them and a pharmaceutical composition for controlling liver disease of human being and animals containing an effective amount sufficient of them having the general formula (I) and an organic acid ester thereof:

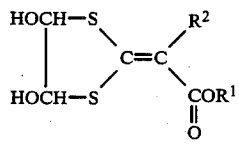

wherein $R^1$ is an alkyl group, a cycloalkyl group, an alkenyl group, an alkynyl group, a benzyl group or an alkoxyalkyl group and $R^2$ is a cyano group, an alkylcarbonyl group, a benzylcarbonyl group, a phenylcarbonyl group, an alkoxycarbonyl group, a cycloalkyloxycarbonyl group, a benzyloxycarbonyl group, an alkenyloxycarbonyl group, an alkynyloxycarbonyl group or an alkoxyalkoxycarbonyl group.

In the above formula (I), the alkyl group of $R^1$, the same group in the alkylcarbonyl group of $R^2$, and the same group in the alkoxycarbonyl group of $R^2$ include a $C_1$–$C_8$ alkyl group, preferably a $C_1$–$C_6$ alkyl group such as methyl, ethyl, n-propyl, iso-propyl, n-butyl, iso-butyl, sec-butyl, tert-butyl, n-pentyl and n-hexyl groups.

The alkenyl group of $R^1$ and the same group in the alkenyloxycarbonyl group of $R^2$ include, for example, allyl, n-buten-2-yl, 2-methyl-3-buten-2-yl, 3-penten-2-yl, 2-methyl-2-propenyl, 2-butenyl, 3-methyl-2-butenyl, 3-methyl-3-butenyl, and 1-methyl-3-butenyl.

The alkynyl group of $R^1$, and the same group in the alkynyloxycarbonyl group of $R^2$ include, for example, propargyl, 2-methyl-3-butyn-2-yl, 2-butynyl, 3-butyn-2-yl, 1-pentyn-3-yl, 3-butynyl, 4-pentyn-2-yl and 4-hexyn-2-yl.

The alkoxyalkyl group of $R^1$, and the same group in alkoxyalkoxycarbonyl group of $R^2$ include an alkoxyalkyl group of which two alkyls may be same as or different from each other and each alkyl is of $C_1$–$C_4$ such as methyl, ethyl, n-propyl, iso-butyl, n-butyl, sec-butyl and tert-butyl.

The compounds represented by the abovementioned general formula (I) and organic acid esters thereof are novel compounds unknown to the literature.

The compounds have actions to activate liver cells and various metabolic functions of liver, and hence they can improve the functions of damaged livers and control liver damages of human being and animals.

The term "controlling liver disease" or the like, referred to in the specification and the claims means to prevent, alleviate or cure various types of liver damage.

The compounds represented by the formula (I) can be synthesized, according to a conventional synthesis process, for example by a way of the reaction schema as shown below:

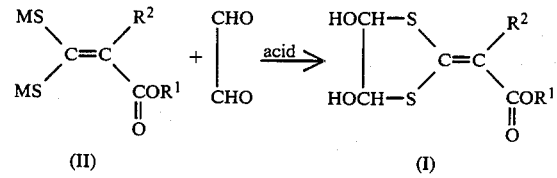

wherein, $R^1$ and $R^2$ are the same as defined above, and M is alkaline metal atom or ammonium group.

That is, according to this process, the compound represented by the formula (I) can be obtained by reacting a compound represented by the formula (II) with glyoxal in the presence of a suitable acid and in an inert solvent.

The acids, which can be used for the above reaction, are, for example, inorganic acids such as sulfuric acid, hydrochloric acid and organic acids such as acetic acid. Particularly acetic acid is advantageous.

As the inert solvents, although water can be used, generally organic-solvents are preferably used.

As the inert organic-solvents, any solvent not seriously disturbing this type of reaction may be used; for example it is possible to use aromatic hydrocarbons such as benzene and toluene, halogenated hydrocarbons such as carbon tetrachloride, chloroform and dichloromethan; ethers such as diethylether, tetrahydrofuran and dioxane; esters such as ethyl acetate; ketones such as acetone, and aprotic solvents such as dimethylformamide and dimethysulfoxide.

In the step of this process, it is preferable that the reaction temperature is below 50° C., particularly a low temperature such as about 15° C.

The reaction can be effected by the use of the both reactants in equimolar ratio, but it is desirable to use glyoxal in slight excess than a compound represented by the formula (II).

The compounds represented by the formula (II) can be synthesized according to the process shown below.

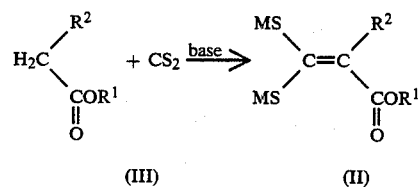

wherein $R^1$, $R^2$ and M are the same as defined above.

That is, the compound represented by the formula (II) can be obtained by reacting a compound represented by the formula (III) with carbon disulfide in the presence of a suitable base.

The bases which can be used for the above reaction are, for example, alkaline metal hydroxides such as sodium hydroxide and potassium hydroxide, alkaline metal carbonate such as potassium carbonate and sodium carbonate, and ammonium hydroxide solution.

The organic acid esters of compounds represented by the formula (I) can be synthesized according to an ordinary esterification process adopted in this chemical reaction field, for example, by a way of the reaction schema as shown below:

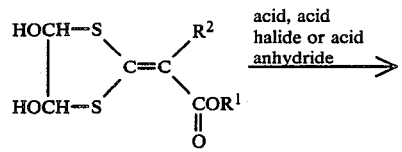

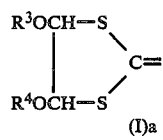

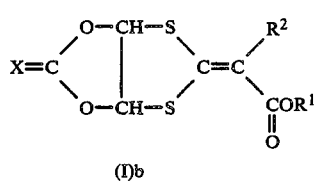

(I)b wherein $R^1$ and $R^2$ are the same as defined above. $R^3$ and $R^4$ which may be same or different, are individually hydrogen, an alkylcarbonyl group, an alkoxycarbonyl group, a mono- or di-alkylcarbamoyl group, a carboxyalkylcarbonyl group, a carboxyalkenylcarbonyl group or a salt thereof except that both $R^3$ and $R^4$ are hydrogen. X is oxygen or sulfur.

That is, according to this ordinary process for estirification, the compound represented by the formula (I)a and (I)b can be obtained by reacting a compound represented by the formula (I) with an acid, an acid halide or an acid anhydride. As the abovementioned acid, acid halide and acid anhydride, the following can be listed: for example, an alkylcarboxylic acid, an organo dibasic acid, carbonic acid and thiocarbonic acid or an acid halide and an acid anhydride thereof, an alkoxycarboxylic acid and a mono- or dialkylcarbamoyl halide and acid halide thereof.

In this invention, the organic acid esters of compounds represented by the formula (I) mean organic acid monoester, organic acid diester and cyclic carbonate derivatives Typical examples of the compounds represented by the formula (I) are shown in Table 1.

TABLE 1

In the formula:

$$\begin{array}{c} HOCH-S \\ | \\ HOCH-S \end{array} \diagdown C=C \diagup \begin{array}{c} R^2 \\ COR^1 \\ \| \\ O \end{array}$$ (I)

| Compound No. | $R^1$ | $R^2$ | Melting point (°C.) or refractive index |
|---|---|---|---|
| 1 | $CH_3$ | $CH_3OC(=O)$ | m.p. 103.5° C. |
| 2 | $C_2H_5$ | $C_2H_5OC(=O)$ | m.p. 87.3° C. |
| 3 | $n\text{-}C_3H_7$ | $n\text{-}C_3H_7OC(=O)$ | m.p. 83.1° C. |

TABLE 1-continued

In the formula:

$$\begin{array}{c} HOCH-S \\ | \\ HOCH-S \end{array} \diagdown C=C \diagup \begin{array}{c} R^2 \\ COR^1 \\ \| \\ O \end{array}$$ (I)

| Compound No. | $R^1$ | $R^2$ | Melting point (°C.) or refractive index |
|---|---|---|---|
| 4 | $n\text{-}C_4H_9$ | $n\text{-}C_4H_9OC(=O)$ | m.p. 51.3° C. |
| 5 | $i\text{-}C_4H_9$ | $i\text{-}C_4H_9OC(=O)$ | m.p. 112.1° C. |
| 6 | $s\text{-}C_4H_9$ | $s\text{-}C_4H_9OC(=O)$ | m.p. 108.3° C. |
| 7 | $t\text{-}C_4H_9$ | $t\text{-}C_4H_9OC(=O)$ | m.p. 122.4° C. |
| 8 | $n\text{-}C_5H_{11}$ | $n\text{-}C_5H_{11}OC(=O)$ | m.p. 60.3° C. |
| 9 | $i\text{-}C_5H_{11}$ | $i\text{-}C_5H_{11}OC(=O)$ | m.p. 78.1° C. |
| 10 | $C_6H_{11}$ | $C_6H_{11}OC(=O)$ | m.p. 173.6° C. |
| 11 | $C_6H_5CH_2$ | $C_6H_5CH_2OC(=O)$ | m.p. 108.3° C. |
| 12 | $CH_2=CHCH_2$ | $CH_2=CHCH_2OC(=O)$ | m.p. 81.2° C. |
| 13 | $CH\equiv C.CH_2$ | $CH\equiv C.CH_2OC(=O)$ | m.p. 64.0° C. |
| 14 | $CH_3OC_2H_4$ | $CH_3OC_2H_4OC(=O)$ | $n_D^{20}$ 1.5733 |
| 15 | $CH_3OCH_2CH(CH_3)$ | $CH_3OCH_2CH(CH_3)OC(=O)$ | $n_D^{20}$ 1.5490 |
| 16 | $CH_3OCH_2CH(C_2H_5)$ | $CH_3OCH_2CH(C_2H_5)OC(=O)$ | $n_D^{20}$ 1.5395 |
| 17 | $n\text{-}C_3H_7$ | $C_2H_5OC(=O)$ | $n_D^{25}$ 1.5450 |
| 18 | $n\text{-}C_4H_9$ | $C_2H_5OC(=O)$ | $n_D^{25}$ 1.5593 |
| 19 | $i\text{-}C_4H_9$ | $C_2H_5OC(=O)$ | $n_D^{25}$ 1.5506 |
| 20 | $n\text{-}C_3H_7$ | $i\text{-}C_3H_7OC(=O)$ | m.p. 109.3° C. |

TABLE 1-continued

In the formula:

$$\begin{array}{c} HOCH-S \\ | \\ HOCH-S \end{array} C=C \begin{array}{c} R^2 \\ COR^1 \\ \| \\ O \end{array} \quad (I)$$

| Compound No. | R¹ | R² | Melting point (°C.) or refractive index |
|---|---|---|---|
| 21 | n-C₄H₉ | i-C₃H₇OC(O)– | m.p. 90.1° C. |
| 22 | i-C₄H₉ | i-C₃H₇OC(O)– | m.p. 110.5° C. |
| 23 | i-C₃H₇ | i-C₃H₇OC(O)– | m.p. 132.6° C. (Remark 4) |
| 24 | CH₃ | CN | m.p. 163.0° C. |
| 25 | C₂H₅ | CN | $n_D^{25}$ 1.5938 |
| 26 | n-C₃H₇ | CN | m.p. 79.8° C. |
| 27 | i-C₃H₇ | CN | m.p. 130.0° C. |
| 28 | n-C₄H₉ | CN | $n_D^{25}$ 1.5705 |
| 29 | i-C₄H₉ | CN | m.p. 110.5° C. |
| 30 | n-C₅H₁₁ | CN | $n_D^{25}$ 1.5679 |
| 31 | i-C₅H₁₁ | CN | $n_D^{25}$ 1.5541 |
| 32 | s-C₅H₁₁ | CN | $n_D^{25}$ 1.5533 |
| 33 | n-C₆H₁₃ | CN | $n_D^{25}$ 1.5462 |
| 34 | CH₃ | –C(O)CH₃ | m.p. 135.3° C. |
| 35 | C₂H₅ | –C(O)CH₃ | m.p. 121.7° C. |
| 36 | n-C₃H₇ | –C(O)CH₃ | m.p. 108.8° C. |
| 37 | i-C₃H₇ | –C(O)CH₃ | m.p. 121.7° C. |
| 38 | n-C₄H₉ | –C(O)CH₃ | m.p. 68.8° C. |
| 39 | i-C₄H₉ | –C(O)CH₃ | m.p. 84.3° C. |
| 40 | s-C₄H₉ | –C(O)CH₃ | m.p. 104.9° C. |
| 41 | t-C₄H₉ | –C(O)CH₃ | m.p. 113.0° C. |
| 42 | n-C₅H₁₁ | –C(O)CH₃ | m.p. 76.2° C. |
| 43 | i-C₅H₁₁ | –C(O)CH₃ | m.p. 82.5° C. |
| 44 | C₆H₅– | –C(O)CH₃ | m.p. 143.8° C. |
| 45 | CH₂=CHCH₂– | –C(O)CH₃ | m.p. 109.3° C. |
| 46 | CH≡C.CH₂– | –C(O)CH₃ | m.p. 118.2° C. |
| 47 | CH₃OC₂H₄– | –C(O)CH₃ | $n_D^{22}$ 1.5742 |
| 48 | C₆H₅CH₂– | –C(O)CH₃ | paste (Remark 1) |
| 49 | C₂H₅ | –C(O)CH₂C₂H₅ | $n_D^{22}$ 1.5889 |
| 50 | C₂H₅ | –C(O)–C₃H₇–n | $n_D^{22}$ 1.5845 |
| 51 | C₂H₅ | –C(O)–C₃H₇–i | $n_D^{22}$ 1.5727 |
| 52 | C₂H₅ | –C(O)–C₄H₉–n | $n_D^{25}$ 1.5828 |
| 53 | C₂H₅ | –C(O)–C₄H₉–i | $n_D^{25}$ 1.5761 |
| 54 | C₂H₅ | –C(O)–C₆H₁₃–n | m.p. 69.0° C. |
| 55 | C₂H₅ | –C(O)–CH₂–C₆H₅ | paste (Remark 2) |
| 56 | C₂H₅ | –C(O)–C₆H₅ | paste (Remark 3) |

Remark 1: NMR $\delta_{CDCl_3}^{TMS}$ ppm; 2.35 (3H, s), 4.0–5.0 (2H, br.), 5.30 (2H, s), 5.6 (2H, br. s), 7.30 (5H, s)
Remark 2: NMR $\delta_{CDCl_3}^{TMS}$ ppm; 1.30 (3H, t), 4.0 (2H, s), 4.1 (2H, q), 3.7–4.5 (2H, br.), 5.3–5.7 (2H, m), 6.9–7.4 (5H, m)
Remark 3: NMR $\delta_{CDCl_3}^{TMS}$ ppm; 0.83 (3H, t), 4.0 (2H, q), 3.7–4.5 (2H, br.), 5.8 (2H, br.s) 7.2–8.0 (5H, m)
Remark 4: NMR $\delta_{TMS}^{CDCl_3}$ ppm; 2.25 (12H, d, J = 7Hz), 3.80 (2H, broad, s), 5.10 (2H, m, J = 7Hz), 5.70 (2H, s)

In the formula 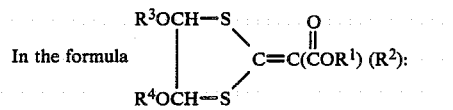 (I)a

| Compound No. | $R^1$ | $R^2$ | $R^3$ | $R^4$ | Melting point (°C.) or refractive index |
|---|---|---|---|---|---|
| 57 | i-$C_3H_7$ | $CO_2C_3H_7$—i | H | $CH_3\overset{O}{\underset{\|\|}{C}}$— | $n_D^{25}$ 1.5352 |
| 58 | i-$C_3H_7$ | $CO_2C_3H_7$—i | $CH_3\overset{O}{\underset{\|\|}{C}}$— | $CH_3\overset{O}{\underset{\|\|}{C}}$— | m.p. 130.0 |
| 59 | n-$C_3H_7$ | $CO_2C_3H_7$—n | $CH_3\overset{O}{\underset{\|\|}{C}}$— | $CH_3\overset{O}{\underset{\|\|}{C}}$— | m.p. 110.6 |
| 60 | sec-$C_4H_9$ | $CO_2C_4H_9$—sec | $CH_3\overset{O}{\underset{\|\|}{C}}$— | $CH_3\overset{O}{\underset{\|\|}{C}}$— | $n_D^{23}$ 1.5126 |
| 61 | n-$C_3H_7$ | $-\overset{O}{\underset{\|\|}{C}}CH_3$ | $CH_3\overset{O}{\underset{\|\|}{C}}$— | $CH_3\overset{O}{\underset{\|\|}{C}}$— | m.p. 151.8 |
| 62 | n-$C_3H_7$ | $CO_2C_3H_7$—n | $(CH_3)_3C\overset{O}{\underset{\|\|}{C}}$— | $(CH_3)_3C\overset{O}{\underset{\|\|}{C}}$— | m.p. 107.6 |
| 63 | n-$C_3H_7$ | $-\overset{O}{\underset{\|\|}{C}}CH_3$ | $(CH_3)_3C\overset{O}{\underset{\|\|}{C}}$— | $(CH_3)_3C\overset{O}{\underset{\|\|}{C}}$— | $n_D^{23}$ 1.4990 |
| 64 | n-$C_3H_7$ | $CO_2C_3H_7$—n | $(CH_3)_2N\overset{O}{\underset{\|\|}{C}}$— | $(CH_3)_2N\overset{O}{\underset{\|\|}{C}}$— | m.p. 129.8 |
| 65 | n-$C_3H_7$ | $-\overset{O}{\underset{\|\|}{C}}CH_3$ | $(CH_3)_2N\overset{O}{\underset{\|\|}{C}}$— | $(CH_3)_2N\overset{O}{\underset{\|\|}{C}}$— | $n_D^{23}$ 1.5581 |
| 66 | n-$C_3H_7$ | $CO_2C_3H_7$—n | $C_2H_5O\overset{O}{\underset{\|\|}{C}}$ | $C_2H_5O\overset{O}{\underset{\|\|}{C}}$ | m.p. 72.0 |
| 67 | n-$C_3H_7$ | $-\overset{O}{\underset{\|\|}{C}}CH_3$ | $C_2H_5O\overset{O}{\underset{\|\|}{C}}$ | $C_2H_5O\overset{O}{\underset{\|\|}{C}}$— | $n_D^{23}$ 1.5243 |
| 68 | n-$C_3H_7$ | $CO_2C_3H_7$—n | $HO_2CC_2H_4\overset{O}{\underset{\|\|}{C}}$— | $HO_2CC_2H_4\overset{O}{\underset{\|\|}{C}}$— | paste (remark 5) |
| 69 | i-$C_3H_7$ | $CO_2C_9H_7$—i | $HO_2CC_2H_4\overset{O}{\underset{\|\|}{C}}$— | $HO_2CC_2H_4\overset{O}{\underset{\|\|}{C}}$— | paste (remark 6) |
| 70 | $CH_3$ | $CO_2CH_3$ | $NaO_2CC_2H_4\overset{O}{\underset{\|\|}{C}}$— | $NaO_2CC_2H_4\overset{O}{\underset{\|\|}{C}}$— | |
| 71 | sec-$C_4H_9$ | $CO_2C_4H_9$—sec | $HO_2CC_2H_4\overset{O}{\underset{\|\|}{C}}$— | $HO_2CC_2H_4\overset{O}{\underset{\|\|}{C}}$— | paste (remark 7) |

Remark 5: NMR $\delta_{CDCl_3}^{TMS}$ ppm; 0.95 (t, 6H), 1.3–2.0 (m, 4H), 2.7 (s, 8H), 4.15 (t, 4H), 6.55 (s, 2H), 10.0–10.5 (br. 2H)
Remark 6: NMR $\delta_{CDCl_3}^{TMS}$ ppm; 1.3 (d, 12H), 2.7 (s, 8H), 5.15 (m, 2H), 6.5 (s, 2H), 8.4 (br. 2H)
Remark 7: NMR $\delta_{CDCl_3}^{TMS}$ ppm; 0.95 (t,6H), 1.30 (d, 6H), 1.4–2.0 (m, 4H), 2.7 (s, 8H), 4.7–5.3 (m, 2H), 6.55 (s, 2H), 9.8–10.5 (br, 2H)

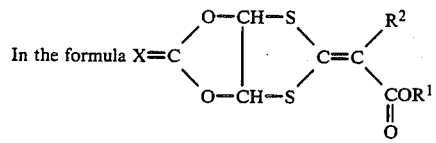 (I)b

In the formula X=C

| Compound No. | X | $R^1$ | $R^2$ | Melting point (°C.) or refractive index |
|---|---|---|---|---|
| 72 | O | $CH_3$ | $CO_2CH_3$ | m.p. 142.7 |
| 73 | O | $C_2H_5$ | $CO_2C_2H_5$ | m.p. 137.3 |
| 74 | O | n-$C_3H_7$ | $CO_2$—n-$C_3H_7$ | m.p. 100.8 |
| 75 | O | iso-$C_3H_7$ | $CO_2$—iso-$C_3H_7$ | m.p. 123.5 |
| 76 | O | n-$C_4H_9$ | $CO_2$—n-$C_4H_9$ | m.p. 58.8 |
| 77 | O | iso-$C_4H_9$ | $CO_2$—iso-$C_4H_9$ | m.p. 104.2 |
| 78 | O | sec-$C_4H_9$ | $CO_2$—sec-$C_4H_9$ | m.p. 93.3 |
| 79 | O | tert-$C_4H_9$ | $CO_2$—tert-$C_4H_9$ | m.p. 140 (Decomposition) |
| 80 | O | n-$C_5H_{11}$ | $CO_2$—n-$C_5H_{11}$ | m.p. 53.4 |
| 81 | O | iso-$C_5H_{11}$ | $CO_2$—iso-$C_5H_{11}$ | m.p. 95.4 |
| 82 | O | $C_6H_5$— | $CO_2$—$C_6H_5$ | m.p. 148.6 |
| 83 | O | $C_6H_5$—$CH_2$— | $CO_2CH_2$—$C_6H_5$ | m.p. 128.1 |
| 84 | O | $CH_2$=$CHCH_2$— | $CO_2CH_2CH$=$CH_2$ | m.p. 93.8 |
| 85 | O | $CH\equiv C.CH_2$— | $CO_2CH_2C\equiv CH$ | $n_D^{20}$ 1.5860 |
| 86 | O | iso-$C_4H_9$ | $CO_2$—iso-$C_3H_7$ | $n_D^{25}$ 1.5348 |
| 87 | O | $CH_3$ | $\overset{O}{\underset{\parallel}{C}}.CH_3$ | m.p. 119.2 |
| 88 | O | $C_2H_5$ | $\overset{O}{\underset{\parallel}{C}}.CH_3$ | m.p. 104.2 |
| 89 | O | iso-$C_3H_7$ | $\overset{O}{\underset{\parallel}{C}}.CH_3$ | $n_D^{19}$ 1.5714 |
| 90 | O | n-$C_3H_7$ | $\overset{O}{\underset{\parallel}{C}}.CH_3$ | m.p. 106.3 |
| 91 | O | n-$C_4H_9$ | $\overset{O}{\underset{\parallel}{C}}.CH_3$ | m.p. 101.1 |
| 92 | O | iso-$C_4H_9$ | $\overset{O}{\underset{\parallel}{C}}.CH_3$ | m.p. 103.2 |
| 93 | O | sec-$C_4H_9$ | $\overset{O}{\underset{\parallel}{C}}.CH_3$ | m.p. 75.6 |
| 94 | O | tert-$C_4H_9$ | $\overset{O}{\underset{\parallel}{C}}.CH_3$ | m.p. 149.0 |
| 95 | O | n-$C_5H_{11}$ | $\overset{O}{\underset{\parallel}{C}}.CH_3$ | m.p. 122.5 |
| 96 | O | i-$C_5H_{11}$ | $\overset{O}{\underset{\parallel}{C}}.CH_3$ | paste (remark 8) |
| 97 | O | $C_6H_5$— | $\overset{O}{\underset{\parallel}{C}}.CH_3$ | m.p. 121.3 |
| 98 | O | $CH_2$=$CHCH_2$— | $\overset{O}{\underset{\parallel}{C}}.CH_3$ | m.p. 114.4 |
| 99 | O | $CH\equiv C.CH_2$— | $\overset{O}{\underset{\parallel}{C}}.CH_3$ | m.p. 146.0 |
| 100 | O | $C_2H_5$ | $-\overset{O}{\underset{\parallel}{C}}.C_2H_5$ | paste (remark 9) |
| 101 | O | $C_2H_5$ | $-\overset{O}{\underset{\parallel}{C}}-C_3H_7$—n | m.p. 89.7 |
| 102 | O | $C_2H_5$ | $-\overset{O}{\underset{\parallel}{C}}-C_3H_7$—i | paste (remark 1) |
| 103 | O | $C_2H_5$ | $-\overset{O}{\underset{\parallel}{C}}-C_4H_9$—n | paste (remark 1) |
| 104 | O | $C_2H_5$ | $-\overset{O}{\underset{\parallel}{C}}-C_4H_9$—i | m.p. 90.2 |
| 105 | O | $C_2H_5$ | $-\overset{O}{\underset{\parallel}{C}}-C_6H_{13}$—n | m.p. 69.5 |
| 106 | O | $C_2H_5$ | $-\overset{O}{\underset{\parallel}{C}}.CH_2$—$C_6H_5$ | paste (remark 12) |
| 107 | s | $C_2H_5$ | $CO_2C_2H_5$ | m.p. 154.8 |
| 108 | s | n-$C_3H_7$ | $CO_2$—$C_3H_7$—n | m.p. 121.1 |
| 109 | s | i-$C_3H_7$ | $CO_2C_3H_7$—i | m.p. 164.2 |
| 110 | s | i-$C_4H_9$ | $CO_2C_4H_9$—i | m.p. 138.5 |
| 111 | s | sec-$C_4H_0$ | $CO_2C_4H_9$—sec | m.p. 164.2 |
| 112 | s | $CH_2$=$CHCH_2$— | $CO_2CH_2CH$=$CH_2$ | m.p. 109.6 |
| 113 | s | $CH\equiv C.CH_2$— | $CO_2CH_2C\equiv CH$ | m.p. 151.0 |

Remark 8: NMR $\delta_{CDCl_3}^{TMS}$ ppm; 0.95 (d, 6H), 1.2-2.0 (m, 3H), 2.36 (s, 3H), 4.3 (t, 2H), 6.5 (s, 2H)
Remark 9: NMR $\delta_{CDCl_3}^{TMS}$ ppm; 1.1 (t, 3H), 1.4 (t, 3H), 2.8 (q, 2H), 4.35 (q, 2H), 6.6 (s, 2H)
Remark 10: NMR $\delta_{CDCl_3}^{TMS}$ ppm; 1.5 (q, 6H) 1.4 (t, 3H), 3.1-3.7 (m, 1H), 4.4 (q, 2H), 6.6 (s, 2H)
Remark 11: NMR $\delta_{CDCl_3}^{TMS}$ ppm; 0.95 (t, 3H), 1.4 (t, 3H), 1.2-2.0 (m, 4H), 2.85 (t, 2H), 4.4 (q, 2H), 6.6 (s, 2H)
Remark 12: NMR $\delta_{CDCl_3}^{TMS}$ ppm; 1.3 (t, 3H), 4.1 (s, 2H), 4.2 (q, 2H), 6.4 (d, 1H), 6.7 (d, 1H), 7.0-7.7 (m, 5H)

The compounds represented by the general formula (I) are low in toxicity to mammals.

Their acute oral toxicities to male rat expressed as $LD_{50}$ values are shown below.

For example, the $LD_{50}$ values of the compound No. 1, No. 2, No. 3, No. 8 and No. 12 are 1,000–3,000 mg/kg, 3,000–5,000 mg/kg, more than 5,000 mg/kg, more than 5,000 mg/kg and 1,000–3,000 mg/kg, respectively.

Particularly, the compounds represented by formula (I) are useful as pharmaceutical for controlling liver damage.

It is well known that liver damages are experimentally, induced by administering chemicals such as carbon tetrachloride and α-naphthyl isothiocyanate to healthy animals.

And it is well known that, bile duct ligation and α-naphthyl isothiocyanate administration induce extra- and intrahepatic cholestasis, respectively, and are similar to the clinical events in human being including the morphological findings.

Accordingly it has any relation with estimating drug used in clinical test that compounds having activity to control liver damage are studied by using a model of liver damage induced by α-naphthylisothiocyanate.

The compounds represented by the formula (I) have activity to prevent lowering liver funcation and improve liver function, by administering orally or parenterally (such as injection) to animals having experimental liver damage.

Accordingly, the compounds are useful as pharmaceutical for human being and animals to prevent and improve liver damages.

That is, the compounds are useful as pharmaceutical for controlling the acute or chronic liver diseases of human being and animals induced by various factors such as alcohols, insufficient nutrision, viruses, chemicals toxicants etc. These factors cause such disease as, for example, hepatitis, liver necrosis, fatty liver, cholestasis and livercirrhosis.

The compounds alone can be used as pharmaceutical for controlling liver diseases.

Otherwise, they may also be formulated, according to usual procedures and means adopted in this field, into pharmaceutical compositions in the form of a mixture with a pharmaceutically acceptable diluent and/or other pharmacologically active substance.

Otherwise, it is also permitted to provide the pharmaceutical of this invention in the form of administration units convenient for their individual application purposes which contain the compound of this invention alone or contain it in mixture with a pharmaceutically acceptable diluent and/or other pharmacologically active substance.

It is also permitted to provide the pharmaceutical of this invention in the form of administration units.

The shape in which the pharmaceutical of this invention can be provided includes, for example, powders, granules, tablets, sugar-coated tablets, pills, capsules, suppositories, suspensions, liquids, emulsions, ampoules, injections, isotonic solutions instillation and the like.

Particularly, the compounds have high water solubility, such as compound No. 23 and No. 12 each dissolve 2000 ppm and 2200 ppm in water at 20° C., compound No. 1 dissolves 2% in 2% gum-arabia aqueous solution.

Then, the compounds are advantageous to use in the administration form of injection and instillation.

This invention includes such mode that the compound of general formula (I) is administered in the form of a mixture with a pharmaceutically acceptable diluent.

The diluent referred to herein mean a material other than the compounds represented by general formula (I). The diluent may be a solid, a semisolid, a liquid or an ingestible capsule.

Examples of the diluent include vehicles, extenders, binders, wetting agents, disintegrators, surfactants, lubricants, dispersants, buffer agents, seasonings, deodorants, dyes, flavors, preservatives, dissolution aids, solvents and like, though these are not limitative.

These diluents may be used either singly or in the form of a mixture of two or more members.

Such pharmaceutically acceptable diluents as above are sometimes used in the form of a mixture with other pharmacologically active substance. Such a use also belongs to the scope of this invention.

The pharmaceutical composition of this invention may be prepared according to any known method. For example, a mixture of the active ingredient and a diluent is formed, for example, into granule, and thus formed granular composition is molded, for example, in tablets.

In case the pharmaceutical composition is for parenteral administration, it is preferable to be made aseptic and, if necessary, be made isotonic to the blood.

Generally, the pharmaceutical composition of this invention contains 0.01%–100% by weight, based on the weight of the composition, of the active compound.

Thus, this invention includes such mode that the said compound is used independently.

In case the compound of this invention is formulated into administration units, individual constituents forming the formulated composition may be either same or different in the shape. Most frequently adopted shapes include, for example, the followings: tablets, granules, pills, powders, sugar-coated tablets, capsules, ampoules, suppositories, suspensions, liquid, emulsion, injection, instillation and the like.

For the control of various liver damages and various diseases derived therefrom, the pharmaceutical composition of the present invention may be applied to human being and animals according to an ordinary procedure adopted in this field, in order to attain such effects as shown in the foresaid animal tests.

Thus, the composition of the present invention is administered orally or parenterally.

The oral administration includes sublingual administration, and the parenteral administration includes administration by way of injection including, for example, subcutaneous, intramuscular and intravenous injections and instillation.

The dose of the pharmaceutical of this invention varies depending on many factors, including the kind of subject (whether the pharmaceutical is administered to human being or to animals, the difference is susceptibility, age, sex, body weight, the clinical picture, the physical conditions of patients, the means of administration, the time and interval of administration, the kind and properties of pharmaceutical composition, the kind of active ingredient, etc.

In some cases, accordingly, the dose of the pharmaceutical may be made, smaller than the minimum dose mentioned below, while in other cases the dose would be in excess of the maximum dose mentioned below.

In case the pharmaceutical is to be administered in a large dose, it is preferable that the pharmaceutical is divisionally administered several times a day.

In the case of oral administration, effective dosage for animals is in the range from 0.1 to 500 mg, preferably from 0.1 to 25 mg, of active ingredient per one kilogramme body weight per day.

In the case of parenteral administration, effective dose for animals is in the range from 0.01 to 250 mg, preferably from 0.1 to 25 mg of active ingredient per one kilogramme body weight per day.

In the case of oral administration, effective dose for human being, deduced from the above-mentioned effective dose for animals with consideration for susceptibility difference and security, is advantageously in the range from 0.1 to 250 mg, preferably from 0.5 to 50 mg, per one kilogramme body weight per day.

In the case of parenteral administration, effective dose for human being is in the range from 0.01 to 100 mg, preferably 0.1 to 25 mg, per kilogramme body weight per day.

Synthesis examples of the compound represented by the formula (I) are shown below.

SYNTHESIS EXAMPLE 1

Synthesis of diisopropyl 4,5-dihydroxy-1,3-dithiolan-2-ylidenemalonate (Compound 23 in Table 1).

A mixture of 56.8 g (0.3 mole) of diisopropyl malonate and 22.8 g (0.3 mole) of carbon disulfide was cooled in cold water, and stirred.

A 40% solution of potassium hydroxide was prepared by dissolving 33.6 g of potassium hydroxide in 50.4 g of water, and 84 g of the solution was dropped into the above-mentioned mixture at a temperature, lower than 20° C., to obtain a solution of dipotassium 2,2-bis(isopropoxycarbonyl)ethylene-1,1-dithiolate.

The dithiolate solution was dropped into a mixture of 44 g of 40% glyoxal, 36 g of acetic acid and 200 ml of benzene with stirring to react them while controlling the dropping so that the mixture was kept at a temperature of lower than 15° C.

After completion of the dropping, the resulting mixture was stirred at room temperature, and the color in red-brown of the mixture was changed to light-yellow. The reaction was completed in one hour.

The benzene layer of the mixture was separated and washed with water. After benzene was removed, a crude crystal was obtained.

The crystal was dried and recrystallized from a mixed solvent of ethylether-n-hexane to obtain 58 g of the intended product;
m.p. 132.6° C.,
NMR $\delta_{TMS}^{CDCl_3}$ ppm: 2.25 (12H, d, J=7 Hz), 3.80 (2H, broad s), 5.10 (2H, m, J=7 Hz), 5.70 (2H, s) yield 60%.

SYNTHESIS EXAMPLE 2

Synthesis of diethyl 4,5-dihydroxy-1,3-dithiolan-2-ylidenemalonate (Compound 2 in Table 1).

A mixture of 16 g (0.1 mole) of diethyl malonate and 7.6 g of carbone disulfide was cooled in ice water and stirred.

24.9 g of 45% aqueous solution of potassium hydroxide was dropped into the above-mentioned mixture at a temperature lower than 20° C. to obtain an aqueous solution of dipotassium 2,2-bis(ethoxycarbonyl)ethylene-1,1-dithiolate.

This aqueous solution of dithiolate was added dropwise to a mixture of 14.5 g of 40% glyoxal, 12 g of acetic acid and 60 ml of benzene with stirring to react them while controlling the dropping so that the mixture was kept at a temperature lower than 15° C.

After completion of the dropping, the resulting mixture was stirred at room temperature, and a color of the mixture was changed from red-brown to light-yellow. The reaction was completed in one hour. The benzene layer of the mixture was separated and washed with water.

After benzene was removed, a crude crystal was obtained.

The crystal was dried and recrystallized from a mixed solvent consisting of ethyl acetate, dichloromethan and n-hexane to obtain 17.8 g of the intended product;
m.p. 87.3° C., yield 60.5%.

SYNTHESIS EXAMPLE 3

Synthesis of diallyl 4,5-dihydroxy-1,3-dithiolan-2-ylidenemalonate (Compound 2 in Table 1).

Similarly to Synthesis Example 2, an aqueous solution of a salt of dithiolate compound was prepared by reacting 6.14 g of diallyl malonate and carbon disulfide with a 45% aqueous solution of potassium hydroxide.

The dithiolate solution was added dropwise into a mixture consisting of 4.8 g of 40% glyoxal, 4.0 g of acetic acid and 30 ml of benzene. The reaction was carried out similarly to Synthesis Example 2 and after treatment was effected. The resultant was recrystallized from dichloromethane-n-hexane to obtain 5.22 g of crystal of the intended product;
m.p. 81.2° C., yield 49%.

SYNTHESIS EXAMPLE 4

Synthesis of bis(3-methoxypropan-2-yl)4,5-dihydroxy-1,3-dithiolan-2-ylidenemalonate (Compound 15 in Table 1).

In a similar way to Synthesis Example 2, the oily intended product is obtained from 8.28 g of bis(3-methoxypropane-2-yl)malonate.

The product was purified through a dry column chromatography of silica gel using the mixed solvent containing ethyl acetate and n-hexane (1:1).

Thus, 3.5 g of the oily intented product was obtained;
$N_D^{20}$ 1.5490, yield 27.4%.

SYNTHESIS EXAMPLE 5

Synthesis of isopropyl 4,5-dihydroxy-1,3-dithiolan-2-ylidenecyanoacetate (Compound 27 in Table 1).

The mixture of 4.24 g (33.3 m. mole) of isopropyl cyanoacetate and, 2.5 g of carbon disulfide was cooled in ice water and stirred.

10.3 g of 36% aqueous solution of patassium hydroxide was dropped into the above-mentioned mixture with taking care so as to keep the mixture at a temperature lower than 20° C. to obtain a solution of dipotassium 2-cyano-2-isopropoxycarbonyl-ethylene-1,1-dithiolate.

The aqueous solution of dithiolate is added dropwise into a mixture consisting of 4.8 g of 40% glyoxal, 4.0 g of acetic acid and 20 ml of benzene with well stirring, while controlling the dropping so that the mixture was kept at a temperature lower than 15° C.

After completion of the dropping, the mixture was stirred at room temperature for 1 hour to complete the reaction.

The resulting reaction mixture is poured into ice water, and then a separated oily product was extracted with dichloromethane.

The organic layer is washed with water, dried and then the solvent was evaporated under reduced pressure. Thus 5.9 g of a crystal of the intended product was obtained;
m.p. 130.0° C.
NMR $\delta_{CDCl_3}^{TMS}$ ppm; 1.30 (6H, d, J=6.2 Hz), 4.5–5.4 (2H, broad), 5.1 (1H, m, J=6.2 Hz), 5.85 (2H, broads) yield 67.7%.

According to the similar way of above Example, Compounds 24–33 in Table 1 can be synthesized.

SYNTHESIS EXAMPLE 6

Synthesis of isopropyl 4,5-dihydroxy-1,3-dithiolan-2-ylideneacetoacetate (Compound 37 in Table 1).

A mixture consisting of 4.81 g (33.3 m. mole) of isopropyl acetoacetate, 2.54 g of carbon disulfide and 10 ml of dimethyl sulfoxide was stirred at room temperature, 4.60 g of powdered anhydrous potassium carbonate was added therein in small portions.

After completion of the adding, the mixture is gradually stirred for 30 minutes at room temperature, thus crimson potassium 2-methylcarbonyl-2-isopropoxy carbonyl ethylene-1,1-dithiolate was obtained.

The dithiolate solution was dropped into a mixture consisting of 4.83 g of 40% glyoxal, 4.0 g of acetic acid and 20 ml of benzene, which had been previously prepared and cooled in ice water and stirred, at a temperature lower than 15° C.

After completion of the dropping, the mixture was stirred for one hour, and the resulting mixture was poured into ice water, and thus an oily product was separated.

The product was extracted with ethyl acetate, washed with water, dried over anhydrous magnesium sulfate and the solvent was evaporated under reduced pressure.

The product was purified through a dry column chromatography using silica gel.

Thus, 1.65 g of the intended compound was obtained; m.p. 121.7° C.

NMR $\delta_{CDCl_3}^{TMS}$ ppm: 1.35 (6H, d, J=6.1 Hz), 2.4 (3H,S), 4.0–4.8 (2H, broad), 5.2 (1H, m, J=6.1 Hz), 5.7 (2H,S) yield 17.9%.

According to the similar way of above Example, Compounds 34–56 in Table 1 can be synthesized.

SYNTHESIS EXAMPLE 7

Synthesis of diisopropyl 4-hydroxy-5-methyl carbonyloxy-1,3-dithiolan-2-ylidenemalonate (Compound 57 in Table 1).

8 g (24.8 m mole) of diisopropyl 4,5-dihydroxy-1,3-dithiolan-2-ylidenemolonate was dissolved in 180 ml of chloroform, and 20 ml of pyridine and 2.53 g (24.8 m mole) of acetic anhydride were added thereto, and then the mixture was stirred for 1 hour at room temperature.

Subsequently, the reaction mixture was poured into ice-water, and was shaked to separate a chloroform layer.

The chloroform layer was washed three times with 1N-hydrochloric acid, and one time with a saturated solution of sodium bicarbonate, and then dried over anhydrous magnesium sulfate, and then chloroform was evaporated to obtain a crude intended product.

The crude intended product was purified through a dry column chromatography using silica gel. Thus, 3.4 g of the oily intended compound was obtained;
refractive index $N_D^{25}$ 1.5325
yield 38%.

SYNTHESIS EXAMPLE 8

Synthesis of di-n-propyl 4,5-bis (N,N-dimethylcarbamoyloxy)-1,3-dithiolane-2-ylidenemalonate (Compound 64 in Table 1)

1.0 g (3.1 m mole) of di-n-propyl 4,5-dihydroxy-1,3-dithiolane-2-ylidenemalonate was dissolved in 5 ml of pyridine, 1.33 g of N,N-dimethylcarbamoyl chloride was dropped into the solution, which was stirred for 18 hours at room temperature.

The reaction mixture was poured into ice-water, extracted with ethyl acetate.

The ethyl acetate layer was washed with 1N-hydrochloric acid and water in order dried over anhydrous magnesium sulfate, and then ethylacetate was evaporated under reduced pressure to obtain a crude intended product.

The crude intended product was recrystallized from solvents consisting of ether-dichloromethanehexane to obtain 1.38 g of crystal of the intended product;
m.p. 129.8° C., yield 96%.

SYNTHESIS EXAMPLE 9

Synthesis of di-sec-butyl 4,5-bis(2'-carboxyethylcarbonyloxy)-1,3-dithiolan-2-ylidenemalonate (Compound 71 in Table 1).

1.0 g (2.85 m mole) of di-sec-butyl 4,5-dihydroxy-1,3-dithiolan-2-ylidenemalonate was dissolved in 5 ml of pyridine and 0.571 g of succinic anhydride was added thereto, then the solution was stirred for 3 days at room temperature.

The reaction mixture was poured into ice-water and extracted with ethyl acetate.

The ethyl acetate layer was washed with 1N-hydrochloric acid and water, and dried over anhydrous magnesium sulfate to obtain 1.57 g of paste of the intended product.
yield 100%.

SYNTHESIS EXAMPLE 10

Synthesis of 7-(methylcarbonyl-tert-butoxycarbonyl)methylene-3-oxo-2,4-dioxa-6,8-dithiabicyclo[3,3,0]octane (Compound 94 in Table 1)

1.0 g (3.4 m mole) of tert-butyl 4,5-dihydroxy-1,3-dithiolane-2-ylidene acetoacetate was dissolved in 150 ml of dichloromethane and 0.93 g of triethylamine was added thereto with cooling by ice-water.

Subsequently a solution consisting of 0.28 ml of trichloromethyl chloroformate and 50 ml of dichloromethane was dropped over 2 hours into the above-mentioned mixture.

After completion of the dropping, the reaction mixture was poured into ice-water, thus the said solvent layer was separated, washed with water and dried over anhydrous magnesium sulfate, and then the solvent was removed to obtain a crude crystal of the intended product.

The crude crystal was recrystallized from a solvent consisting of ether-hexane to obtain 1.0 g crystal of the intended product;
m.p. 149° C., yield 92%.

SYNTHESIS EXAMPLE 11

Synthesis of 7-bis(allyloxy carbonyl)methylene-3-thioxo-2,4-dioxa-6,8-dithiabicyclo[3,3,0]octane (Compound 112 in Table 1)

0.1 g (3.1 m mole) of diallyl 4,5-dihydroxy-1,3-dithiolan-2-ylidene malonate was dissolved in 150 ml of dichloromethane, and 0.73 g of triethylamine was was added thereto with cooling by ice-water.

Subsequently a solution consisting of 0.26 ml of thiophosgene and 50 ml of dichloramethane was dropped during 2 hours into the above-mentioned mixture.

After completion of the dropping, according to the way of Synthesis Example 10, 1.15 g crystal of the intended product is obtained;
m.p. 109.6° C., yield 100%.

Examples of the present invention are illustrated below, in which all parts are by weight. The kind and the ratio of components may be varied.

EXAMPLE 1

| Compound 22 | 10 parts |
|---|---|
| Heavy magnesium oxide | 10 parts |
| Lactose | 80 parts |

The above-mentioned components were homogeneously mixed and pulverized to obtain a powder or a granule.

EXAMPLE 2

| Compound 26 | 10 parts |
|---|---|
| Synthetic aluminum silicate | 10 parts |
| Calcium hydrogenphosphate | 5 parts |
| Lactose | 75 parts |

The above-mentioned components were treated in the same way as in Example 1 to obtain a powder.

EXAMPLE 3

| Compound 3 | 50 parts |
|---|---|
| Starch | 10 parts |
| Lactose | 15 parts |
| Crystalline cellulose | 20 parts |
| Polyvinyl alcohol | 5 parts |
| Water | 30 parts |

The above-mentioned components were homogeneously kneaded, granulated, dried and sieved to obtain a granule.

EXAMPLE 4

99 Parts of the granule obtained in Example 3 was incorporated with 1 part of calcium stearate, and then subjected to compression molding to obtain a tablet 10 mm in diameter.

EXAMPLE 5

| Compound 6 | 95 parts |
|---|---|
| Polyvinyl alcohol | 5 parts |
| Water | 30 parts |

The above-mentioned components were treated in the same manner as in Example 3 to obtain a granule.

90 Parts of the thus obtained granule was incorporated with 10 parts of crystalline cellulose, and then subjected to compression molding to obtain a tablet 8 mm in diameter.

Further, this tablet was formed into a sugar-coated tablet by use of proper amounts of a suspension comprising ethanolic shellac, syrup gelation and precipitated calcium carbonate, and a dye.

EXAMPLE 6

| Compound 45 | 0.5 parts |
|---|---|
| Nonionic surfactant | 2.5 parts |
| Isotonic sodium chloride solution | 97 parts |

The above-mentioned components were mixed together with heating to form a solution, which was then cooled to obtain an injection.

EXAMPLE 7

The powder obtained in Example 1 is filled into commercially available capsules to obtain a capsule.

TEST EXAMPLE 1

Protective (Controlling) Effect on liver damage induced by carbon tetrachloride.

Carbon tetrachloride administration induces centrilobular necrosis of the liver associated with loss of diphosphopyridine nucleotide, hepatic glycogen, coenzyme A and increase in neutral fat. Release of several enzymes from the hepatocytes, and increases of enzyme activities in the plasma are recognized as the result of the damage of the liver.

A suitable means for evaluating the degree induced by carbon tetrachloride or the degree of protection afforded by drugs is to study the plasma glutamic-pyruvic transaminase (p-GPT) activity.

Method

The test compounds were dissolved or suspended in olive oil or diethyleneglycol and administered orally at the dose of 250 mg/kg to the mice (Six-week-old male mice-dd strain).

After 6 hours, carbon tetrachloride was administered orally 0.05 ml/kg.

Animals were killed 24 hours after carbon tetrachloride administration, and the liver was grossly observed.

The plasma was obtained by centrifugation. Activity of p-GPT were determined by the method of Reitman and Frankel and expressed in Karmen units.

Score for liver damage index was as follows:

| Liver damage index | Description |
|---|---|
| 0 | Normal |
| 2 | Slightly recognized |
| 4 | Clearly observable damage |
| 6 | Heavy damage |

1 Each figure indicated average of 5 mice.

The result is shown in Table 2,

Results

TABLE 2

Protective Effect on liver damage induced by carbon tetrachloride

| Compound No. | Liver Damage Index | p-GPT |
|---|---|---|
| Carbon Tetrachloride alone | 5.0 | >2,100 |
| Control | 0.0 | 12 |
| 1 | 0.0 | 23 |
| 2 | 0.0 | 15 |
| 3 | 0.2 | 12 |
| 4 | 0.0 | 18 |
| 5 | 0.0 | 135 |
| 6 | 0.0 | 21 |
| 7 | 0.0 | 90 |
| 8 | 0.0 | 21 |
| 9 | 0.0 | 47 |
| 10 | 0.0 | 72 |
| 11 | 0.0 | 33 |
| 12 | 1.0 | 63 |
| 13 | 0.0 | 30 |
| 14 | 0.2 | 56 |
| 15 | 0.0 | 39 |
| 16 | 0.2 | 30 |

TABLE 2-continued

Protective Effect on liver damage induced by carbon tetrachloride

| Compound No. | Liver Damage Index | p-GPT |
|---|---|---|
| 17 | 0.6 | 40 |
| 18 | 0.0 | 28 |
| 19 | 0.4 | 9 |
| 20 | 0.4 | 30 |
| 21 | 0.0 | 9 |
| 22 | 0.0 | 9 |
| Control | 0.0 | 36.0 |
| 23 | 0.0 | 22.5 |
| Control | 0.0 | 11.7 |
| 24 | 1.0 | 152 |
| 25 | 2.0 | |
| 26 | 0.0 | 24 |
| 27 | 0.2 | 23 |
| 28 | 0.4 | 80 |
| 29 | 1.0 | 175 |
| 30 | 0.6 | 116 |
| 31 | 0.6 | 105 |
| 32 | 0.0 | 35 |
| 33 | 0.8 | 93 |
| 34 | 0.0 | 31 |
| 35 | 0.0 | 92 |
| 36 | 0.2 | 30 |
| 37 | 0.4 | 149 |
| 38 | 0.0 | 31 |
| 39 | 0.2 | 19 |
| 40 | 0.4 | 172 |
| 41 | 0.6 | 105 |
| 42 | 0.0 | 31 |
| 43 | 0.2 | 36 |
| 44 | 0.4 | 73 |
| 45 | 0.0 | 13 |
| 46 | 0.0 | 16 |
| 47 | 0.2 | 25 |
| 48 | 0.0 | 18 |
| 49 | 0.4 | 23 |
| 50 | 1.2 | 75 |
| 51 | 1.6 | 172 |
| 52 | 0.4 | 25 |
| 53 | 0.8 | 94 |
| 54 | 2.6 | 188 |
| 55 | 1.8 | 105 |
| 56* | 4.0 | >1418 |
| 57 | 1.0 | 262.0 |
| 58 | 1.0 | 42.0 |
| 59 | 0.4 | 40.9 |
| 60 | 0 | 203.0 |
| 61 | 0.8 | 1260 |
| 62 | 1.2 | 223.2 |
| 63 | 1.8 | 402.6 |
| 64 | 3.4 | |
| 65 | 1.6 | 498.7 |
| 66 | 0.2 | 53.8 |
| 67 | 0.8 | 127.7 |
| 68 | 2.0 | |
| 69 | 2.2 | |
| 70 | 1.2 | 121.0 |
| 71 | 2.2 | |
| 72 | 0 | 32.3 |
| 73 | 0.8 | 75.1 |
| 74 | 0 | 38.8 |
| 75 | 0.2 | 19.9 |
| 76 | 0.6 | 84.8 |
| 77 | 0.2 | 21.2 |
| 78 | 0 | 96.0 |
| 79 | 0.8 | 66.0 |
| 80 | 0.4 | 71.1 |
| 81 | 1.2 | 108.1 |
| 82 | 0.4 | 159.7 |
| 83 | 1.2 | 105.5 |
| 84 | 0 | 13.9 |
| 85 | 0 | 30.3 |
| 86 | 0.6 | >436.4 |
| 87 | 0.6 | 45.7 |
| 88 | 1.4 | 211.6 |
| 89 | 0.4 | 26.3 |
| 90 | 0.3 | 23.2 |
| 91 | 0.8 | 27.9 |
| 92 | 0.8 | 29.4 |
| 94 | 0.8 | 26.5 |
| 95 | 0.8 | 28.2 |
| 96 | 0 | 15.4 |
| 97 | 0 | 12.5 |
| 98 | 0 | 16.9 |
| 99 | 0 | 18.4 |
| 101 | 0.2 | 20.0 |
| 102 | 1.2 | 48.5 |
| 103 | 0 | 14.7 |
| 104 | 0 | 17.6 |
| 105 | 1.6 | 107.4 |
| 106 | 1.0 | 602.2 |
| 112 | 0.6 | 20.2 |
| Control | 0 | 29.5 |
| 107 | 0.6 | 42.6 |
| 108 | 0 | 31.0 |
| 109 | 0.4 | 139.3 |
| 110 | 1.2 | 554.7 |
| 111 | 0.8 | 18.6 |
| 113 | 0.6 | 13.3 |

*Compound 56 was administered at 100 mg/kg.

As shown in Table 2, the compounds of the resent invention remarkably improved liver damage index and p-GPT activity, as compared with the plot of carbon tetrachloride alone. Accordingly the compounds have pretective effect on liver damage.

TEST EXAMPLE 2

Protective effect on liver damage induced by α-naphthyl isothiocyanate (referred to as "ANIT", hereinafter).

It is well known that experimental cholestasis is accomplished by administration with ANIT in mice and rats, and studied as a cholestasis model in human being.

ANIT and CCl₄ induce necrosis in the liver. ANIT causes it as small focci in perilobular parenchyna and CCl₄ causes centrilobular parenchymal coagulation necrosis. Therefore, both compounds elevate p-GPT activities, but the degree of the elevation is significantly defferent from each other.

From these information, the elevation of plasma GPT activity in these models are thought to have defferent characteristics.

METHOD 1

Test compounds, dissolved or suspended in olive oil or diethyleneglycol, were orally administered 2 times at intervals of 3 hrs to mice at the dose of 250 mg/kg. At 3 hrs after the second administration with test compounds, ANIT was administered orally at 35 mg/kg.

Mice were sacrificed at 24 hrs after ANIT administration and blood samples were collected. The blood samples were centrifuged and plasma was obtained.

Plasma GPT activity and alkaline phosphatase activity were determined by Reitman & Frankel's method and Bessey-Lowry's method, respectively. The activity was expressed with Karmen Unit and Bessey-Lowry Unit, respectively.

Result

The result is shown in Tables 3-1 and 3-2.

TABLE 3-1

| | Protective effect on liver damage induced by ANIT | |
|---|---|---|
| Compound No. | p-GPT (K.U.) | Alkaline phosphatase activity (B-L.V.) |
| Control | 7.4 | 3.3 |
| ANIT alone | 324.0 | 5.3 |
| 1 | 128.0 | 3.9 |
| 2 | 28.0 | 4.4 |
| 3 | 53.0 | 4.7 |
| 4 | 26.8 | 3.3 |
| 6 | 142.0 | 4.9 |
| 8 | 56.0 | 4.3 |
| 12 | 19.9 | 4.9 |
| 17 | 242.0 | 4.8 |
| 18 | 180.8 | 4.8 |
| 19 | 170.5 | 5.1 |
| 20 | 163.4 | 4.0 |
| 21 | 293.1 | 4.5 |
| 22 | 221.0 | 5.0 |
| 23 | 76.0 | 4.0 |

TABLE 3-2

| | Protective effect on liver damage induced by ANIT | |
|---|---|---|
| Compound No. | p-GPT (K.U.) | Alkaline phosphatase activity (B-L.V.) |
| ANIT alone | >653.7 | 5.3 |
| 5 | 134.8 | 3.5 |
| 7 | 422.8 | 3.5 |
| 9 | 27.2 | 3.4 |
| 10 | 363.7 | 4.9 |
| 11 | 437.5 | 4.3 |
| 13 | 265.6 | 4.5 |
| 14 | 11.5 | 3.1 |
| 15 | 134.5 | 3.7 |
| 16 | 275.2 | 5.0 |
| Compound A* | >755.0 | 8.5 |

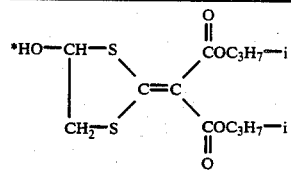

*

As shown in Tables 3-1 and -2, test compounds supressed the elevation of plasma GPT and alkaline phosphatase activities with ANIT administration in mice.

Accordingly the compounds have protective effect on cholestatic liver injury.

METHOD 2

Test compounds, dissolved or suspended in olive oil or diethyleneglycol, were orally administered at the dose of 250 mg/kg to the mice (Six or Seven-week-old male mice-dd strain).

After 6 hours, ANIT dissolved in olive oil, was aministered orally at 35 mg/kg.

Mice were sacrificed at 24 hours after ANIT administration and blood samples were collected. The blood samples were centrifuged and plasma was obtained.

Plasma GPT activity and alkaline phosphatase activity were determined by Reitman & Frankel's method and Bessey-Lowry's method, respectively.

The activity was expressed with Karmen Unit and Bessey-Lowry Unit, respectively.

Result

The result is shown in Table 3-3 and Table 3-4.

TABLE 3-3

| | Protective effect on liver damage induced by ANIT | |
|---|---|---|
| Compound No. | p-GPT (K.U.) | Alkaline phosphatase activity (B-L.V.) |
| Control | 17.5 | 2.9 |
| ANIT alone | >460.2 | >9.6 |
| 34 | 32.7 | 4.2 |
| 35 | >245.0 | 4.6 |
| 36 | 60.0 | 3.9 |
| 37 | 177.4 | 4.4 |
| 38 | 29.4 | 5.3 |
| 39 | 70.7 | 6.8 |
| 40 | 272.5 | 5.2 |
| 41 | 132.7 | 6.0 |
| 42 | 30.8 | 4.8 |
| 43 | 298.9 | 5.9 |
| 44 | 140.2 | 5.1 |
| 45 | 136.9 | 5.6 |
| 46 | 29.9 | 5.3 |
| 47 | 40.1 | 4.2 |
| 48 | 36.8 | 4.1 |

TABLE 3-4

| | Protective effect on liver damage induced by ANIT | |
|---|---|---|
| Compound No. | p-GPT (K.U.) | Alkaline phosphatase activity (B-L.V.) |
| Control | 11.3 | 3.7 |
| ANIT alone | 300.3 | 4.5 |
| 50 | 18.5 | 3.0 |
| 52 | 24.1 | 3.8 |

As shown in Tables 3-3 and -4, test compounds supressed the elevation of plasma GPT and alkaline phosphatase activities with ANIT administration in mice.

Accordinly the compounds have protective effect on cholestatic liver injury.

TEST EXAMPLE 3

Protective Effect on Fatty Liver

Carbon tetrachloride also induces fatty liver. Carbon tetrachloride is generally considered to damage microsome and thereby to inhibit protein synthesis and induce fatty liver.

Method

Carbon tetrachloride was subcutaneously administered to 5–6 week-old male rats (SD strain) for 4 days at the dose of 0.5 ml/kg/day.

Simultaneously, the compound of the present invention was orally administered to the rats for 4 days at the dose of 30 mg/kg/day or 100 mg/kg/day.

On the 5th day, the rats were sacrificed by exsanguination.

The controlling (protective) effect was evaluated by determining the content of triglyceride in the liver.

Triglyceride was determined colorimetrically by chromotropic acid method.

The result is shown in Table 4. Each value represented the percentage of mean value in carbon tetrachloride alone group.

Result

TABLE 4

| Compound No. | Controlling (protective) effect on fatty liver | |
|---|---|---|
| | Dose mg/kg | Triglyceride |
| Carbon tetrachloride alone | — | 100 |
| Control | — | 32.0 |
| 1 | 100 | 57.5 |
| 2 | 100 | 46.6 |
| 3 | 100 | 39.0 |
| 5 | 100 | 40.0 |
| 12 | 100 | 35.4 |

What is claimed is:

1. A dithiolane represented by the formula (I):

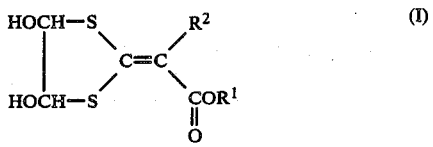

wherein $R^1$ is a $C_1$–$C_8$ alkyl group, a cyclohexyl group, a $C_3$–$C_5$ alkenyl group, a $C_3$–$C_6$ alkynyl group, a benzyl group or a $C_2$–$C_8$ alkoxyalkyl group and $R^2$ is a cyano group, a $C_2$–$C_9$ alkylcarbonyl group, a benzylcarbonyl group, a phenylcarbonyl group, a $C_2$–$C_9$ alkoxycarbonyl group, a cyclohexyloxycarbonyl group, a benzyloxycarbonyl group, a $C_4$–$C_6$ alkenyloxycarbonyl group, a $C_4$–$C_7$ alkynyloxycarbonyl group or a $C_3$–$C_9$ alkoxyalkoxycarbonyl group;

or an organic acid ester thereof which ester is:

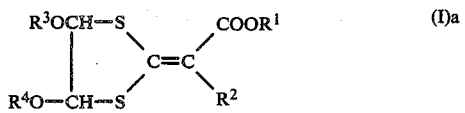

or

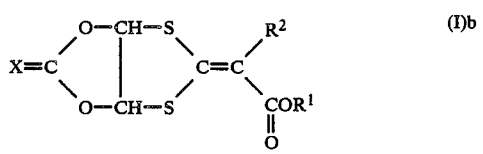

wherein $R^1$ and $R^2$ are the same as defined above; $R^3$ and $R^4$, which may be same or different, are individually hydrogen, a $C_2$–$C_7$ alkylcarbonyl group, a $C_2$–$C_5$ alkoxycarbonyl group, a $C_2$–$C_9$ mono or di-alkylcarbamoyl group, a $C_3$–$C_6$ carboxyalkylcarbonyl group, a $C_4$–$C_7$ carboxyalkenylcarbonyl group, or a salt thereof, provided that $R^3$ and $R^4$ are not both hydrogen; and X is oxygen or sulfur.

2. A dithiolane according to claim 1, wherein the compound represented by the formula (I) is:

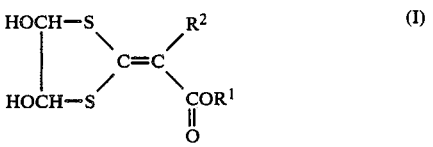

wherein $R^1$ is a $C_1$–$C_8$ alkyl group, a cyclohexyl group, a $C_3$–$C_5$ alkenyl group, a $C_3$–$C_6$ alkynyl group, a benzyl group or a $C_2$–$C_8$ alkoxyalkyl group and $R^2$ is a cyano group, a $C_2$–$C_9$ alkylcarbonyl group, a benzylcarbonyl group, a phenylcarbonyl group, a $C_2$–$C_9$ alkoxycarbonyl group, a cyclohexyloxycarbonyl group, a benzyloxycarbonyl group, a $C_4$–$C_6$ alkenyloxycarbonyl group, a $C_4$–$C_7$ alkynyloxycarbonyl group or a $C_3$–$C_9$ alkoxyalkoxycarbonyl group.

3. Diethyl 4,5-dihydroxy-1,3 dithiolan-2-ylidenemalonate.

4. Diisopropyl 4,5-dihydroxy-1,3-dithiolan-2-ylidenemalonate.

5. Methoxyethyl 4,5-dihydroxy-1,3-dithiolan-2-ylideneacetoacetate.

6. Benzyl 4,5-dihydroxy-1,3-dithiolan-2-ylideneacetoacetate.

7. Ethyl 4,5-dihydroxy-1,3-dithiolan-2-ylidene isovalerylacetate.

8. Diisopropyl 4,5-bis(methylcarbonyloxy)-1,3-dithiolan-2-ylidenemalonate.

9. 7-bis(iso-propoxycarbonyl)methylene-2,4-dioxa-6,8-dithia-3-oxo-bicyclo[3,3,0]octane.

10. A pharmaceutical composition for controlling liver damage, comprising a pharmaceutically acceptable diluent and an effective amount of a dithiolane compound represented by the formula (I):

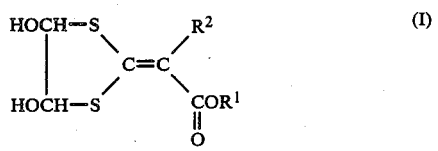

wherein $R^1$ is a $C_1$–$C_8$ alkyl group, a cyclohexyl group, a $C_3$–$C_5$ alkenyl group, a $C_3$–$C_6$ alkynyl group, a benzyl group or a $C_2$–$C_8$ alkoxyalkyl group and $R^2$ is a cyano group, a $C_2$–$C_9$ alkylcarbonyl group, a benzylcarbonyl group, a phenylcarbonyl group, a $C_2$–$C_9$ alkoxycarbonyl group, a cyclohexyloxycarbonyl group, a benzyloxycarbonyl group, a $C_4$–$C_6$ alkenyloxycarbonyl group, a $C_4$–$C_7$ alkynyloxycarbonyl group or a $C_3$–$C_9$ alkoxyalkoxycarbonyl group; or an organic acid ester thereof which ester is:

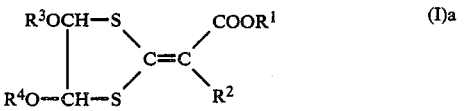

or

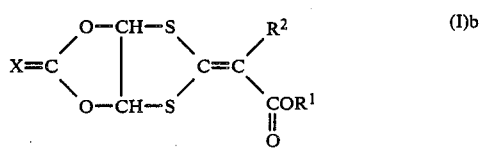

wherein $R^1$ and $R^2$ are the same as defined above; $R^3$ and $R^4$, which may be same or different, are individually hydrogen, a $C_2$–$C_7$ alkylcarbonyl group, a $C_2$–$C_5$ alkoxycarbonyl group, a $C_2$–$C_9$ mono or di-alkylcarbamoyl group, a $C_3$–$C_6$ carboxyalkylcarbonyl group, a $C_4$–$C_7$ carboxyalkenylcarbonyl group, or a salt thereof, provided that $R^3$ and $R^4$ are not both hydrogen; and X is oxygen or sulfur.

11. A pharmaceutical composition according to claim 10, wherein compound represented by the formula (I) is:

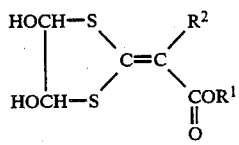

wherein $R^1$ is a $C_1$–$C_8$ alkyl group, a cyclohexyl group, a $C_3$–$C_5$ alkenyl group, a $C_3$–$C_6$ alkynyl group, a benzyl group or a $C_2$–$C_8$ alkoxyalkyl group and $R^2$ is a cyano group, a $C_2$–$C_9$ alkylcarbonyl group, a benzylcarbonyl group, a phenylcarbonyl group, a $C_2$–$C_9$ alkoxycarbonyl group, a cyclohexyloxycarbonyl group, a benzyloxycarbonyl group, a $C_4$–$C_6$ alkenyloxycarbonyl group, a $C_4$–$C_7$ alkynyloxycarbonyl group or a $C_3$–$C_9$ alkoxyalkoxycarbonyl group.

12. A pharmaceutical composition according to claim 10, wherein the said liver damage is hepatitis.

13. A pharmaceutical composition according to claim 10, wherein the said liver damage is fatty liver.

14. A pharmaceutical composition according to claim 10, wherein the said liver damage is cholestasis.

15. A pharmaceutical composition according to claim 10, wherein the compound is formulated into a dosage unit form.

16. The pharmaceutical composition according to claim 15, wherein the dosage unit form is selected from the group consisting of a powder, granule, tablet, pill, sugar-coated tablet, capsule, ampoule, suppository, suspension, liquid, emulsion, injection and instillation.

17. The pharmaceutical composition according to claim 10, wherein the dosage unit form is injection or instillation.

18. The pharmaceutical composition according to claim 10, wherein the said compound is diethyl 4,5-dihydroxy-1,3-dithiolan-2-ylidenemalonate.

19. The pharmaceutical composition according to claim 10, wherein the said compound is diisopropyl 4,5-dihydroxy-1,3-dithiolan-2-ylidenemalonate.

20. The pharmaceutical composition according to claim 10, wherein the said compound is methoxyethyl 4,5-dihydroxy-1,3-dithiolan-2-ylideneacetoacetate.

21. The pharmaceutical composition according to claim 10, wherein the said compound is benzyl 4,5-dihydroxy-1,3-dithiolan-2-ylidene acetoacetate.

22. The pharmaceutical composition according to claim 10, wherein the said compound is ethyl 4,5-dihydroxy-1,3-dithiolan-2-ylideneisovalerylacetate.

23. The pharmaceutical composition according to claim 10, wherein the said compound is diisopropyl 4,5-bis(methylcarbonyloxy)-1,3-dithiolan-2-ylidenemalonate.

24. The pharmaceutical composition according to claim 10 wherein the said compound is 7-bis(isopropoxycarbonyl)methylene-2,4-dioxa-6,8-dithia-3-oxo-bicyclo[3,3,0]octane.

25. A process for producing a dithiolane compound represented by the formula (I):

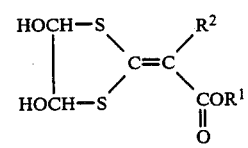

wherein $R^1$ is a $C_1$–$C_8$ alkyl group, a cyclohexyl group, a $C_3$–$C_5$ alkenyl group, $C_3$–$C_6$ a alkynyl group, a benzyl group or a $C_2$–$C_8$ alkoxyalkyl group and $R^2$ is a cyano group, a $C_2$–$C_9$ alkylcarbonyl group, a benzylcarbonyl group, a phenylcarbonyl group, a $C_2$–$C_9$ alkoxycarbonyl group, a cyclohexyloxycarbonyl group, a benzyloxycarbonyl group, a $C_4$–$C_6$ alkenyloxycarbonyl group, a $C_4$–$C_7$ alkynyloxycarbonyl group, or a $C_3$–$C_9$ alkoxyalkoxycarbonyl group, or an organic acid ester thereof, which process comprises reacting a compound represented by the formula (II):

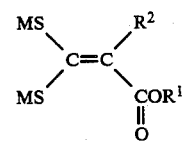

wherein $R^1$ and $R^2$ are the same as defined above and M is alkali metal atom or ammonium group, with glyoxal in the presence of an acid, and optionally, further reacting said compound represented by the formula (I) with acid, acid halide or acid anhydride to obtain a compound represented by the formula (I)a:

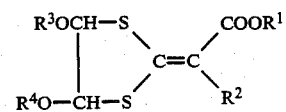

wherein $R^1$ and $R^2$ are the same as defined above, $R^3$ and $R^4$, which may be same or different, are individually hydrogen, a $C_2$–$C_7$ alkylcarbonyl group, a $C_2$–$C_5$ alkoxycarbonyl group, a $C_2$–$C_9$ mono- or dialkylcarbamoyl group, a $C_3$–$C_6$ carboxyalkylcarbonyl group, a $C_4$–$C_7$ carboxyalkenylcarbonyl group, or a salt thereof, provided that $R^3$ and $R^4$ are not both hydrogen, or reacting said compound represented by the formula (I) with phosgene or thiophosgene to obtain a compound represented by the formula (I)b:

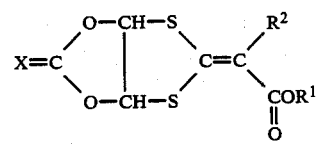

wherein $R^1$ and $R^2$ are the same as defined above and X is oxygen or sulfur.

26. A process according to claim 25, wherein said reaction from the compound of formula (II) to the compound of formula (I) is carried out in the presence of an acid.

27. A process according to claim 26, wherein said acid is an organic acid.

28. A process according to claim 27, wherein said organic acid is acetic acid.

29. A process according to claim 10, wherein said reaction from the compound of formula (II) to the compound of formula (I) is carried out at a temperature below 50° C.

30. A process according to claim 29, wherein said temperature is in the range of −10° C. to 10° C.

31. A process according to claim 10, wherein said reaction from the compound of formula (II) to the compound of formula (I)a is carried out in the presence of a base.

32. A process according to claim 31, wherein said base is an organic base.

33. A process according to claim 32, wherein said organic base is pyridine or triethylamine.

34. A process according to claim 10, wherein said reaction from the compound of formula (I) to the compound of the formula (I)a is carried out at a temperature in the range of from −10° C. to room temperature.

35. A process according to claim 10, wherein said acid, acid halide and acid anhydride used in the reaction from the compound of formula (I) to the compound of the formula (I)a are an alkylcarboxylic acid or a dibasic acid, a halide thereof, an anhydride thereof, a halide of an alkoxycarboxylic acid or a halide of a mono- di-alkylcarbamic acid.

36. A process according to claim 10, wherein trichloromethyl chloroformate is used in place of phosgene used in the reaction from the compound of the formula (I) to the compound of the formula (I)b.

37. A process according to claim 10, wherein said reaction from the compound of formula (I) to the compound of formula (I)b is carried out in the presence of a base.

38. A process according to claim 37, wherein said base is an organic base.

39. A process according to claim 38, wherein said organic base is pyridine or triethylamine.

40. A process according to claim 10, wherein said reaction from the compound of formula (I) to the compound of formula (I)b is carried out at a temperature in the range of from −10° C. to room temperature.

* * * * *